(12) United States Patent
Tunheim et al.

(10) Patent No.: US 9,261,461 B2
(45) Date of Patent: Feb. 16, 2016

(54) SYSTEMS AND METHODS FOR MONITORING OIL/GAS SEPARATION PROCESSES

(75) Inventors: Ola Tunheim, Bryne (NO); Robert P. Freese, Pittsboro, NC (US); James Robert MacLennan, Aberdeen (GB)

(73) Assignee: Halliburton Energy Services, Inc., Houston, TX (US)

( * ) Notice: Subject to any disclaimer, the term of this patent is extended or adjusted under 35 U.S.C. 154(b) by 481 days.

(21) Appl. No.: 13/618,662

(22) Filed: Sep. 14, 2012

(65) Prior Publication Data
US 2013/0032736 A1    Feb. 7, 2013

Related U.S. Application Data

(63) Continuation-in-part of application No. 13/616,106, filed on Sep. 14, 2012, which is a continuation-in-part of application No. 13/198,915, filed on Aug. 5, 2011, and a continuation-in-part of application No.
(Continued)

(51) Int. Cl.
*G01N 21/85* (2006.01)

(52) U.S. Cl.
CPC ..................................... *G01N 21/85* (2013.01)

(58) Field of Classification Search
CPC . E21B 43/255; G01N 21/636; G01N 21/8507
USPC .................................................. 166/250.01
See application file for complete search history.

(56) References Cited

U.S. PATENT DOCUMENTS

| 5,431,227 | A | 7/1995 | Montgomery et al. |
| 5,540,825 | A | 7/1996 | Yeung et al. |
| 5,680,900 | A | 10/1997 | Nguyen et al. |
| 5,737,076 | A | 4/1998 | Glaus et al. |
| 5,996,690 | A | 12/1999 | Shaw et al. |
| 6,016,191 | A | 1/2000 | Ramos et al. |

(Continued)

FOREIGN PATENT DOCUMENTS

| EP | 1969326 | 9/2008 |
| EP | 2087328 | 8/2009 |

(Continued)

OTHER PUBLICATIONS

International Search Report and Written Opinion for PCT/US2013/058864 dated Dec. 16, 2013.
(Continued)

*Primary Examiner* — Zakiya W Bates
*Assistant Examiner* — Ashish Varma
(74) *Attorney, Agent, or Firm* — McDermott Will & Emery LLP; Scott Brown

(57) ABSTRACT

Disclosed are systems and methods for analyzing an oil/gas separation process. One disclosed system includes a flow path containing a fluid, a fluid separator coupled to the flow path and having an inlet for receiving the fluid and a discharge conduit for discharging the fluid after having undergone a separation process in the fluid separator, an optical computing device having an integrated computational element configured to optically interact with the fluid before the fluid enters the fluid separator and after the fluid exits the fluid separator and thereby generate optically interacted light, and at least one detector arranged to receive the optically interacted light and generate an output signal corresponding to a characteristic of the fluid.

23 Claims, 3 Drawing Sheets

Related U.S. Application Data

13/198,950, filed on Aug. 5, 2011, and a continuation-in-part of application No. 13/198,972, filed on Aug. 5, 2011, and a continuation-in-part of application No. 13/204,005, filed on Aug. 5, 2011, and a continuation-in-part of application No. 13/204,046, filed on Aug. 5, 2011, and a continuation-in-part of application No. 13/204,123, filed on Aug. 5, 2011, now Pat. No. 8,960, 294, and a continuation-in-part of application No. 13/204,165, filed on Aug. 5, 2011, and a continuation-in-part of application No. 13/204,213, filed on Aug. 5, 2011, and a continuation-in-part of application No. 13/204,294, filed on Aug. 5, 2011.

(56) References Cited

U.S. PATENT DOCUMENTS

| | | |
|---|---|---|
| 6,198,531 B1 | 3/2001 | Myrick et al. |
| 6,268,911 B1 | 7/2001 | Tubel et al. |
| 6,529,276 B1 | 3/2003 | Myrick |
| 6,729,400 B2 | 5/2004 | Mullins et al. |
| 6,755,978 B2 | 6/2004 | Oddie |
| 6,880,566 B2 | 4/2005 | Newman |
| 7,123,844 B2 | 10/2006 | Myrick |
| 7,138,156 B1 | 11/2006 | Myrick et al. |
| 7,236,237 B2 | 6/2007 | Schmilovitch et al. |
| 7,332,094 B2 | 2/2008 | Abney et al. |
| 7,472,748 B2 | 1/2009 | Gdanski et al. |
| 7,623,233 B2 | 11/2009 | Freese et al. |
| 7,671,973 B2 | 3/2010 | Van Beek et al. |
| 7,697,141 B2 | 4/2010 | Jones et al. |
| 7,712,527 B2 | 5/2010 | Roddy |
| 7,789,171 B2 | 9/2010 | Grayson et al. |
| 7,834,312 B2 | 11/2010 | Lievois et al. |
| 7,834,999 B2 | 11/2010 | Myrick et al. |
| 7,911,605 B2 | 3/2011 | Myrick et al. |
| 7,920,258 B2 | 4/2011 | Myrick et al. |
| 7,934,556 B2 | 5/2011 | Clark et al. |
| 8,049,881 B2 | 11/2011 | Myrick et al. |
| 8,141,633 B2 | 3/2012 | Hampton et al. |
| 8,253,619 B2 | 8/2012 | Holbrook et al. |
| 8,345,234 B2 | 1/2013 | Myrick et al. |
| 8,547,556 B2 | 10/2013 | Irani |
| 8,780,352 B2 | 7/2014 | Freese et al. |
| 8,823,939 B2 | 9/2014 | Freese et al. |
| 8,879,053 B2 | 11/2014 | Freese et al. |
| 8,908,165 B2 | 12/2014 | Tunheim et al. |
| 8,912,477 B2 | 12/2014 | Freese et al. |
| 8,941,046 B2 | 1/2015 | Freese et al. |
| 8,960,294 B2 | 2/2015 | Freese et al. |
| 8,997,860 B2 | 4/2015 | Freese et al. |
| 9,013,698 B2 | 4/2015 | Freese et al. |
| 9,013,702 B2 | 4/2015 | Freese et al. |
| 9,019,501 B2 | 4/2015 | Freese et al. |
| 9,074,990 B2 | 7/2015 | Freese et al. |
| 9,080,943 B2 | 7/2015 | Freese et al. |
| 2001/0020675 A1 | 9/2001 | Tubel et al. |
| 2001/0023614 A1 | 9/2001 | Tubel et al. |
| 2002/0023752 A1 | 2/2002 | Qu et al. |
| 2002/0109080 A1 | 8/2002 | Tubel et al. |
| 2003/0056581 A1 | 3/2003 | Turner et al. |
| 2003/0143580 A1 | 7/2003 | Straus |
| 2003/0145988 A1 | 8/2003 | Mullins et al. |
| 2004/0045705 A1 | 3/2004 | Gardner et al. |
| 2004/0129884 A1 | 7/2004 | Boyle et al. |
| 2004/0179194 A1 | 9/2004 | Schmilovitch et al. |
| 2006/0102343 A1 | 5/2006 | Skinner et al. |
| 2006/0142955 A1 | 6/2006 | Jones et al. |
| 2006/0158734 A1 | 7/2006 | Schuurmans et al. |
| 2007/0095528 A1 | 5/2007 | Ziauddin et al. |
| 2007/0114372 A1 | 5/2007 | Lievois et al. |
| 2007/0177240 A1 | 8/2007 | Van Beek et al. |
| 2007/0215385 A1 | 9/2007 | Anderson |
| 2007/0281870 A1 | 12/2007 | Robb et al. |
| 2007/0282647 A1 | 12/2007 | Freese et al. |
| 2007/0291251 A1 | 12/2007 | Rensen et al. |
| 2008/0000635 A1 | 1/2008 | Rioufol et al. |
| 2008/0041594 A1 | 2/2008 | Boles et al. |
| 2008/0094623 A1 | 4/2008 | Schuurmans et al. |
| 2008/0133193 A1 | 6/2008 | Gdanski et al. |
| 2008/0166720 A1 | 7/2008 | Hsieh et al. |
| 2008/0217011 A1 | 9/2008 | Pauls et al. |
| 2008/0231849 A1 | 9/2008 | Myrick et al. |
| 2008/0262737 A1 | 10/2008 | Thigpen et al. |
| 2008/0276687 A1 | 11/2008 | Myrick et al. |
| 2008/0309930 A1 | 12/2008 | Rensen |
| 2009/0002697 A1 | 1/2009 | Freese et al. |
| 2009/0015819 A1 | 1/2009 | Van Beek et al. |
| 2009/0033933 A1 | 2/2009 | Myrick et al. |
| 2009/0073433 A1 | 3/2009 | Myrick et al. |
| 2009/0087912 A1 | 4/2009 | Ramos et al. |
| 2009/0097024 A1 | 4/2009 | Blackburn et al. |
| 2009/0140144 A1 | 6/2009 | Myrick et al. |
| 2009/0154288 A1 | 6/2009 | Heathman |
| 2009/0182693 A1 | 7/2009 | Fulton et al. |
| 2009/0205821 A1 | 8/2009 | Smith |
| 2009/0216504 A1 | 8/2009 | Priore et al. |
| 2009/0219512 A1 | 9/2009 | Myrick et al. |
| 2009/0219538 A1 | 9/2009 | Myrick et al. |
| 2009/0219539 A1 | 9/2009 | Myrick et al. |
| 2009/0219597 A1 | 9/2009 | Myrick et al. |
| 2009/0245718 A1 | 10/2009 | Li et al. |
| 2009/0250613 A1 | 10/2009 | Myrick et al. |
| 2009/0299946 A1 | 12/2009 | Myrick et al. |
| 2009/0305330 A1 | 12/2009 | Kroon et al. |
| 2009/0316150 A1 | 12/2009 | Myrick et al. |
| 2010/0006292 A1 | 1/2010 | Boles et al. |
| 2010/0042348 A1 | 2/2010 | Bakker |
| 2010/0050905 A1 | 3/2010 | Lewis et al. |
| 2010/0051266 A1 | 3/2010 | Roddy et al. |
| 2010/0051275 A1 | 3/2010 | Lewis et al. |
| 2010/0073666 A1 | 3/2010 | Perkins et al. |
| 2010/0084132 A1 | 4/2010 | Noya et al. |
| 2010/0141952 A1 | 6/2010 | Myrick et al. |
| 2010/0148785 A1* | 6/2010 | Schaefer .................. G01V 8/02 324/338 |
| 2010/0149523 A1 | 6/2010 | Heideman et al. |
| 2010/0149537 A1 | 6/2010 | Myrick et al. |
| 2010/0153048 A1 | 6/2010 | Myrick et al. |
| 2010/0182600 A1 | 7/2010 | Freese et al. |
| 2010/0195105 A1 | 8/2010 | Myrick et al. |
| 2010/0245096 A1 | 9/2010 | Jones et al. |
| 2010/0265509 A1 | 10/2010 | Jones et al. |
| 2010/0269579 A1 | 10/2010 | Lawrence et al. |
| 2010/0285105 A1 | 11/2010 | Radianingtyas |
| 2010/0302539 A1 | 12/2010 | Myrick et al. |
| 2010/0305741 A1 | 12/2010 | Myrick |
| 2010/0326659 A1 | 12/2010 | Schultz et al. |
| 2010/0328669 A1 | 12/2010 | Myrick et al. |
| 2011/0042320 A1 | 2/2011 | Allen |
| 2011/0048708 A1 | 3/2011 | Glasbergen et al. |
| 2011/0163046 A1 | 7/2011 | Neal et al. |
| 2011/0166046 A1* | 7/2011 | Weaver .................... C02F 1/325 507/101 |
| 2011/0197662 A1* | 8/2011 | McAlister .............. G01N 1/405 73/61.59 |
| 2011/0199610 A1 | 8/2011 | Myrick et al. |
| 2011/0212512 A1 | 9/2011 | Wang et al. |
| 2011/0312012 A1 | 12/2011 | Skinderso et al. |
| 2012/0000643 A1 | 1/2012 | Bruun et al. |
| 2012/0135396 A1 | 5/2012 | McDevitt et al. |
| 2012/0150451 A1 | 6/2012 | Skinner et al. |
| 2012/0160329 A1 | 6/2012 | MacKenzie et al. |
| 2012/0250017 A1 | 10/2012 | Morys et al. |
| 2013/0031964 A1 | 2/2013 | Tunheim et al. |
| 2013/0031970 A1 | 2/2013 | Freese et al. |
| 2013/0031971 A1 | 2/2013 | Freese et al. |
| 2013/0031972 A1 | 2/2013 | Freese et al. |
| 2013/0032333 A1 | 2/2013 | Freese et al. |
| 2013/0032340 A1 | 2/2013 | Freese et al. |
| 2013/0032344 A1 | 2/2013 | Freese et al. |
| 2013/0032345 A1 | 2/2013 | Freese et al. |
| 2013/0033701 A1 | 2/2013 | Tunheim et al. |

(56) References Cited

U.S. PATENT DOCUMENTS

| | | | |
|---|---|---|---|
| 2013/0033702 A1 | 2/2013 | Tunheim et al. | |
| 2013/0034842 A1 | 2/2013 | Tunheim et al. | |
| 2013/0284895 A1 | 10/2013 | Freese et al. | |
| 2014/0263974 A1 | 9/2014 | Freese et al. | |

FOREIGN PATENT DOCUMENTS

| | | | |
|---|---|---|---|
| EP | 2140238 | | 1/2010 |
| EP | 2320027 | A1 | 5/2011 |
| FR | 2954563 | A1 | 6/2011 |
| GB | 2353310 | A | 2/2001 |
| JP | 2009284813 | A | 12/2009 |
| WO | 9850680 | A2 | 11/1998 |
| WO | 2004018840 | A1 | 3/2004 |
| WO | 2006137902 | A2 | 12/2006 |
| WO | 2007064575 | | 6/2007 |
| WO | 2006137902 | A3 | 12/2007 |
| WO | 2008121715 | A1 | 10/2008 |
| WO | 2009055200 | A2 | 4/2009 |
| WO | 2009055220 | A2 | 4/2009 |
| WO | 2009077758 | A1 | 6/2009 |
| WO | 2011063086 | A1 | 5/2011 |
| WO | 2014042909 | A1 | 3/2014 |
| WO | 2014042933 | A1 | 3/2014 |
| WO | 2014043010 | A1 | 3/2014 |
| WO | 2014043050 | A1 | 3/2014 |
| WO | 2014043057 | A1 | 3/2014 |

OTHER PUBLICATIONS

International Preliminary Report on Patentability for PCT/US2012/046892 dated Feb. 20, 2014.
International Search Report and Written Opinion for PCT/US2012/044148 dated Oct. 4, 2012.
Official Action for Australian Patent Application 2012294881 dated May 22, 2014.
Myrick, et al. "Spectral Tolerance Determination for Multivariate Optical Element Design," Fresenuis' Journal of Analytical Chemistry, 369:2001; pp. 351-355.
Gdanski et al., "A New Model for Matching Fracturing Fluid Flowback Composition," 2007 SPE Hydraulic Fracturing Technology Conference held in College Station, Texas, SPE 106040.
Gdanski et al., "Using Lines-of-Solutions to Understand Fracture Conductivity and Fracture Cleanup," SPE Production and Operations Symposium held in Oklahoma City, OK, 2011, SPE 142096.
Ramachandran et al., "Chemical Kinetics in Real Time: Using the Differential Rate Law and Discovering the Reaction Orders," A Physical chemistry Laboratory Experiment, Journal of chemical Education; 1996, pp. 686-689.
International Search Report and Written Opinion for PCT/US2013/057832 dated Nov. 22, 2013.
International Search Report and Written Opinion for PCT/US2012/047065 dated Jul. 16, 2013.
International Search Report and Written Opinion for PCT/US2012/045677 dated Jul. 16, 2013.
International Search Report and Written Opinion for PCT/US2012/046898 dated Apr. 5, 2013.
International Search Report and Written Opinion for PCT/US2013/058041 dated Dec. 2, 2013.
International Search Report and Written Opinion for PCT/US2013/058700 dated Dec. 6, 2013.
International Search Report and Written Opinion for PCT/US2013/058855 dated Dec. 17, 2013.
Official Action for New Zealand Patent Application No. NZ 704529 dated Jun. 9, 2015.
Official Action for Canadian Patent Application No. CA 2,842,191 dated May 6, 2015.
Official Action for Australian Patent Application No. 2013252855 dated Apr. 15, 2015.
Dai et al., Molecular Factor Computing for Predictive Spectroscopy, Pharmaceutical Research, vol. 24, No. 8, 2007, pp. 1441-1449.
Mendendorp J., et al., Application of Integrated Sensing and Processing in Spectroscopic Imaging and Sensing, Journal of Chemometrics, vol. 19, 2005, pp. 533-542.
Official Action for Singapore Patent Application No. 11201500780V dated Jun. 16, 2015.
Official Action for Australian Patent Application No. 2013 252841 dated Nov. 10, 2014.
Official Action for Australian Patent Application No. 2013 252881 dated Nov. 12, 2014.

\* cited by examiner

SYSTEMS AND METHODS FOR MONITORING OIL/GAS SEPARATION PROCESSES

CROSS-REFERENCE TO RELATED APPLICATIONS

The present application claims priority to and is a continuation-in-part application of co-owned U.S. patent application Ser. No. 13/616,106 filed on Sep. 14, 2012, which is a continuation-in-part application of U.S. patent application Ser. Nos. 13/198,915; 13/198,950; 13/198,972; 13/204,005; 13/204,046; 13/204,123; 13/204,165; 13/204,213; and 13/204,294, each of which were filed on Aug. 5, 2011. The contents of each priority application are hereby incorporated by reference.

BACKGROUND

The present invention relates to optical analysis systems and methods for analyzing fluids and, in particular, to systems and methods for analyzing an oil/gas separation process.

Most hydrocarbon-bearing reservoirs produce a mixture of oil and/or gas together with water, usually in the form of brine, and large amounts of dissolved minerals or precipitates, mostly common salts. In fact, in some oil wells, water and other by-products can amount to as much as eighty to ninety percent of the total production yield. This is particularly true during the later stages of production. Somewhere in the production process the produced mixture undergoes a separation process where the oil/gas is separated from the remaining components of the mixture and subsequently delivered to a refinery for treatment. The water and remaining components are usually removed from the hydrocarbons using one or more single phase or multi-phase separation devices. Generally, these devices operate to agglomerate and coalesce the produced hydrocarbons, thereby separating them from the water and other components of the produced mixture.

In some cases, the separated water and other components are able to be pumped back into the ground, perhaps in some borehole neighboring the one from which it was removed. This process simply replaces a portion of the liquid removed from the reservoir, but also simultaneously serves to maintain required formation pressures for efficient production rates. In offshore applications, it is often desirable to discharge the produced water directly into the surrounding ocean, thereby eliminating the expense of pumping the fluid back downhole.

Before the water can be discharged into the ocean, however, or any other body of water (e.g., rivers, lakes, streams, etc. in other applications) it must first be rigorously tested to make sure that it does not contain any oil or other impurities that could damage the surrounding sea life. As environmental regulations increasingly become more stringent with respect to the disposal of produced water into the ocean, it becomes increasingly crucial to obtain accurate and timely analysis of the separated fluids so as to not be exposed to undesirable and unnecessary fines and/or fees.

SUMMARY OF THE INVENTION

The present invention relates to optical analysis systems and methods for analyzing fluids and, in particular, to systems and methods for analyzing an oil/gas separation process.

In some aspects of the disclosure, a system is disclosed. The system may include a flow path containing a fluid, a fluid separator coupled to the flow path and having an inlet for receiving the fluid and a discharge conduit for discharging the fluid after having undergone a separation process in the fluid separator, an optical computing device having an integrated computational element configured to optically interact with the fluid before the fluid enters the fluid separator and after the fluid exits the fluid separator and thereby generate optically interacted light, and at least one detector arranged to receive the optically interacted light and generate an output signal corresponding to a characteristic of the fluid.

In other aspects of the disclosure, a method of determining a characteristic of a fluid is disclosed. The method may include containing a fluid within a flow path, conveying the fluid to a fluid separator coupled to the flow path, the fluid separator having an inlet for receiving the fluid and a discharge conduit for discharging the fluid after having undergone a separation process in the fluid separator, arranging at least one optical computing device on the fluid separator, the at least one optical computing device having at least one integrated computational element and at least one detector arranged therein, optically interacting the at least one integrated computational element with the fluid at or near the inlet, thereby generating a first beam of optically interacted light corresponding to the characteristic of the fluid at or near the inlet, optically interacting the at least one integrated computational element with the fluid at or near the discharge conduit, thereby generating a second beam of optically interacted light corresponding to the characteristic of the fluid at or near the discharge conduit, receiving the first and second beams of optically interacted light with the at least one detector, and generating an output signal with the at least one detector, the output signal being indicative of how the characteristic of the fluid changes between the inlet and the discharge conduit.

The features and advantages of the present invention will be readily apparent to those skilled in the art upon a reading of the description of the preferred embodiments that follows.

BRIEF DESCRIPTION OF THE DRAWINGS

The following figures are included to illustrate certain aspects of the present invention, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
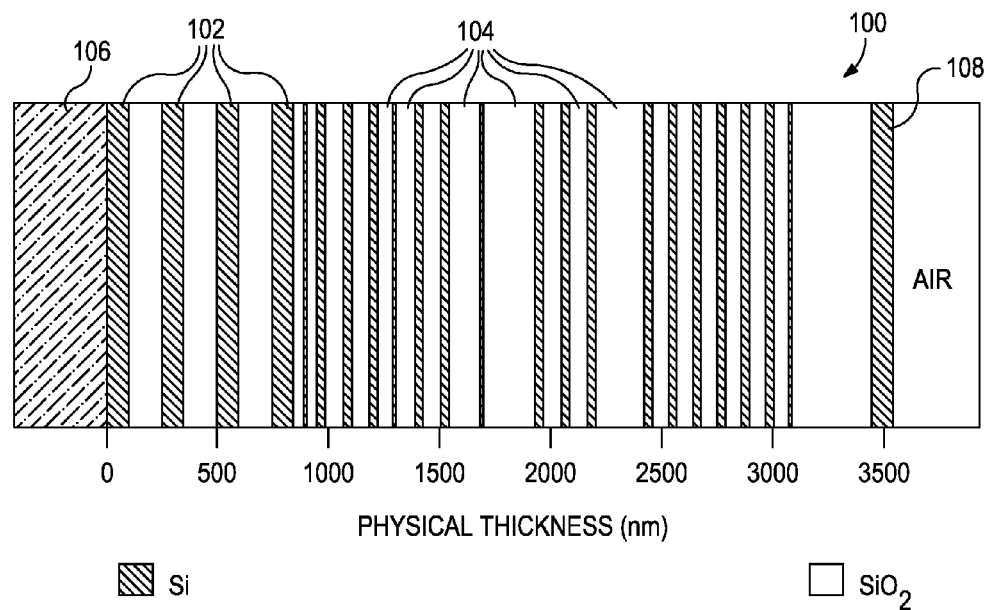
FIG. 1 illustrates an exemplary integrated computation element, according to one or more embodiments.

The present invention relates to optical analysis systems and methods for analyzing fluids and, in particular, to systems and methods for analyzing an oil/gas separation process.

The exemplary systems and methods described herein employ various configurations of optical computing devices, also commonly referred to as "opticoanalytical devices," for the real-time or near real-time monitoring of fluids. In operation, the systems and methods disclosed herein may be useful and otherwise advantageous in determining the quality of a fluid in fluid separation processes. For example, the optical computing devices disclosed herein, which are described in more detail below, can advantageously provide real-time or near real-time monitoring of fluid flow and fluid separation processes that cannot presently be achieved with either onsite analyses at a job site or via more detailed analyses that take place in a laboratory. A significant and distinct advantage of these devices is that they can be configured to specifically detect and/or measure a particular component or characteristic of interest of a fluid, such as a known adulterant, thereby allowing qualitative and/or quantitative analyses of the fluid to occur without having to undertake a time-consuming sample processing procedure. With real-time or near real-time analyses on hand, the exemplary systems and methods described herein may be able to provide some measure of proactive or responsive control over the fluid flow and fluid separation processes, enable the collection and archival of fluid information in conjunction with operational information to optimize subsequent operations, and/or enhance the capacity for remote job execution.

Those skilled in the art will readily appreciate that the systems and methods disclosed herein may be suitable for use in the oil and gas industry since the described optical computing devices provide a relatively low cost, rugged, and accurate means for monitoring hydrocarbon quality in order to facilitate the efficient management of oil/gas production. It will be appreciated, however, that the various disclosed systems and methods are equally applicable to other technology fields including, but not limited to, the food and drug industry, industrial applications, mining industries, or any field where it may be advantageous to determine in real-time or near real-time the concentration or a characteristic of a specific substance in a flowing fluid. In at least one embodiment, for example, the present systems and methods may be employed to monitor the quality of potable water after the water has undergone one or more separation processes to remove contaminants or adulterants therefrom. In other embodiments, the present systems and methods may be employed in the military or security fields, such as in submarines or other water craft. In yet other embodiments, the present systems and methods may prove useful in the trucking and auto industries.

The optical computing devices suitable for use in the present embodiments can be deployed at two or more fluidly communicable points within a flow path, such as a fluid separation device or separator. In some embodiments, for example, the optical computing devices may be employed at both the inlet and discharge locations of a fluid separator in order to monitor the conditions of the incoming and outgoing fluid and, therefore, the overall effectiveness of the separator. In operation, the optical computing device arranged at the discharge location may be configured to ensure a proper or environmentally safe chemical composition of the fluid upon its discharge from the separator. Depending on the location of the particular optical computing device, various types of information about the fluid can be obtained. In some cases, for instance, the optical computing devices can be used to monitor changes to the fluid as a result of adding a treatment substance thereto, removing a treatment substance therefrom in a separator, or exposing the fluid to a condition that potentially changes a characteristic of the fluid in some way. Thus, the systems and methods described herein may be configured to monitor a flow of fluids and, more particularly, to monitor the fluid upon its discharge from a separator.

As used herein, the term "fluid" refers to any substance that is capable of flowing, including particulate solids, liquids, gases, slurries, emulsions, powders, muds, glasses, combinations thereof, and the like. In some embodiments, the fluid can be an aqueous fluid, including water or the like. In some embodiments, the fluid can be a non-aqueous fluid, including organic compounds, more specifically, hydrocarbons, oil, a refined component of oil, petrochemical products, and the like. In some embodiments, the fluid can be a treatment fluid or a formation fluid. Fluids can include various flowable mixtures of solids, liquids and/or gases. Illustrative gases that can be considered fluids according to the present embodiments include, for example, air, nitrogen, carbon dioxide, argon, helium, methane, ethane, butane, and other hydrocarbon gases, combinations thereof and/or the like.

As used herein, the term "characteristic" refers to a chemical, mechanical, or physical property of a substance. A characteristic of a substance may include a quantitative value of one or more chemical components therein. Such chemical components may be referred to herein as "analytes." Illustrative characteristics of a substance that can be monitored with the optical computing devices disclosed herein can include, for example, chemical composition (e.g., identity and concentration in total or of individual components), impurity content, pH, viscosity, density, ionic strength, total dissolved solids, salt content, porosity, opacity, bacteria content, combinations thereof, and the like.

As used herein, the term "flow path" refers to a route through which a fluid is capable of being transported between two points. In some cases, the flow path need not be continuous or otherwise contiguous between the two points. Exemplary flow paths include, but are not limited to, a flowline, a pipeline, a hose, a fluid separator, a process facility, a storage vessel, combinations thereof, or the like. In cases where the flow path is a pipeline, or the like, the pipeline may be a pre-commissioned pipeline or an operational pipeline. In other cases, the flow path may be created or generated via movement of an optical computing device through a fluid (e.g., an open air sensor). In yet other cases, the flow path is not necessarily contained within any rigid structure, but refers to the path fluid takes between two points, such as where a fluid flows from one location to another without being contained, per se. It should be noted that the term flow path does not necessarily imply that a fluid is flowing therein, rather that a fluid is capable of being transported or otherwise flowable therethrough.

As used herein, the term "substance," or variations thereof, refers to at least a portion of a material of interest to be evaluated using the optical computing devices described herein. In some embodiments, the substance is the characteristic of interest, as defined above, and may include any integral component of the fluid flowing within the flow path. In other embodiments, the substance may be a material of interest flowing jointly with and otherwise separate from the fluid.

As used herein, the term "electromagnetic radiation" refers to radio waves, microwave radiation, infrared and near-infrared radiation, visible light, ultraviolet light, X-ray radiation and gamma ray radiation.

As used herein, the term "optical computing device" refers to an optical device that is configured to receive an input of electromagnetic radiation from a substance, and produce an output of electromagnetic radiation from a processing element arranged within the optical computing device. The processing element may be, for example, an integrated computational element (ICE) used in the optical computing device.

As discussed in greater detail below, the electromagnetic radiation that optically interacts with the processing element is changed so as to be readable by a detector, such that an output of the detector can be correlated to at least one characteristic of interest being measured or monitored in the fluid. The output of electromagnetic radiation from the processing element can be reflected electromagnetic radiation, transmitted electromagnetic radiation, and/or dispersed electromagnetic radiation. Whether reflected or transmitted electromagnetic radiation is analyzed by the detector may be dictated by the structural parameters of the optical computing device as well as other considerations known to those skilled in the art. In addition, emission and/or scattering of the substance, for example via fluorescence, luminescence, Raman scattering, and/or Raleigh scattering, can also be monitored by the optical computing devices.

As used herein, the term "optically interact" or variations thereof refers to the reflection, transmission, scattering, diffraction, or absorption of electromagnetic radiation either on, through, or from one or more processing elements (i.e., integrated computational elements). Accordingly, optically interacted light refers to electromagnetic radiation that has been reflected, transmitted, scattered, diffracted, or absorbed by, emitted, or re-radiated, for example, using the integrated computational elements, but may also apply to interaction with a fluid or a substance in the fluid.

The exemplary systems and methods described herein will include at least two optical computing devices strategically arranged along a flow path, such as a fluid separator, in order to monitor the concentration of one or more substances or characteristics of interest in the fluid and verify any concentration differences between measurement or monitoring locations. Each optical computing device may include an electromagnetic radiation source, at least one processing element (e.g., integrated computational elements), and at least one detector arranged to receive optically interacted light from the at least one processing element. As disclosed below, however, in at least one embodiment, the electromagnetic radiation source may be omitted and instead the electromagnetic radiation may be derived from the fluid or substance itself. In some embodiments, the exemplary optical computing devices may be specifically configured for detecting, analyzing, and quantitatively measuring a particular characteristic or analyte of interest of the fluid in the flow path. In other embodiments, the optical computing devices may be general purpose optical devices, with post-acquisition processing (e.g., through computer means) being used to specifically detect the characteristic of the sample.

In some embodiments, suitable structural components for the exemplary optical computing devices are described in commonly owned U.S. Pat. Nos. 6,198,531; 6,529,276; 7,123,844; 7,834,999; 7,911,605, 7,920,258, and 8,049,881, each of which is incorporated herein by reference in its entirety, and U.S. patent application Ser. Nos. 12/094,460; 12/094,465; and 13/456,467, each of which is also incorporated herein by reference in its entirety. As will be appreciated, variations of the structural components of the optical computing devices described in the above-referenced patents and patent applications may be appropriate, without departing from the scope of the disclosure, and therefore, should not be considered limiting to the various embodiments disclosed herein.

The optical computing devices described in the foregoing patents and patent applications combine the advantage of the power, precision and accuracy associated with laboratory spectrometers, while being extremely rugged and suitable for field use. Furthermore, the optical computing devices can perform calculations (analyses) in real-time or near real-time without the need for time-consuming sample processing. In this regard, the optical computing devices can be specifically configured to detect and analyze particular characteristics and/or analytes of interest of a fluid or a substance in the fluid. As a result, interfering signals are discriminated from those of interest in the substance by appropriate configuration of the optical computing devices, such that the optical computing devices provide a rapid response regarding the characteristics of the fluid or substance as based on the detected output. In some embodiments, the detected output can be converted into a voltage that is distinctive of the magnitude of the characteristic being monitored in the fluid. The foregoing advantages and others make the optical computing devices particularly well suited for field and downhole use, but may equally be applied to other industries or technologies where accurate monitoring of fluid flow is desirable.

The optical computing devices can be configured to detect not only the composition and concentrations of a substance in a fluid, but they also can be configured to determine physical properties and other characteristics of the substance as well, based on their analysis of the electromagnetic radiation received from the substance. For example, the optical computing devices can be configured to determine the concentration of an analyte and correlate the determined concentration to a characteristic of a substance by using suitable processing means. As will be appreciated, the optical computing devices may be configured to detect as many characteristics or analytes as desired for a given substance or fluid. All that is required to accomplish the monitoring of multiple characteristics or analytes is the incorporation of suitable processing and detection means within the optical computing device for each characteristic or analyte. In some embodiments, the properties of the substance can be a combination of the properties of the analytes therein (e.g., a linear, non-linear, logarithmic, and/or exponential combination). Accordingly, the more characteristics and analytes that are detected and analyzed using the optical computing devices, the more accurately the properties or concentration of the given substance will be determined.

The optical computing devices described herein utilize electromagnetic radiation to perform calculations, as opposed to the hardwired circuits of conventional electronic processors. When electromagnetic radiation interacts with a substance, unique physical and chemical information about the substance may be encoded in the electromagnetic radiation that is reflected from, transmitted through, or radiated from the substance. This information is often referred to as the spectral "fingerprint" of the substance. The optical computing devices described herein are capable of extracting the information of the spectral fingerprint of multiple characteristics or analytes within a substance and converting that information into a detectable output regarding the overall properties of the substance. That is, through suitable configurations of the optical computing devices, electromagnetic radiation associated with characteristics or analytes of interest in a substance can be separated from electromagnetic radiation associated with all other components of the substance in order to estimate the properties of the substance in real-time or near real-time.

As briefly mentioned above, the processing elements used in the exemplary optical computing devices described herein may be characterized as integrated computational elements (ICE). Each ICE is capable of distinguishing electromagnetic radiation related to the characteristic or analyte of interest from electromagnetic radiation related to other components of a substance. Referring to FIG. 1, illustrated is an exemplary ICE 100 suitable for use in the optical computing devices used in the systems and methods described herein. As illustrated, the ICE 100 may include a plurality of alternating layers 102 and 104, such as silicon (Si) and $SiO_2$ (quartz), respectively. In general, these layers 102, 104 consist of materials whose index of refraction is high and low, respectively. Other examples might include niobia and niobium, germanium and germania, MgF, SiO, and other high and low index materials known in the art. The layers 102, 104 may be strategically deposited on an optical substrate 106. In some embodiments, the optical substrate 106 is BK-7 optical glass. In other embodiments, the optical substrate 106 may be another type of optical substrate, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite the optical substrate 106 in FIG. 1), the ICE 100 may include a layer 108 that is generally exposed to the environment of the flow path, device, or installation. The number of layers 102, 104 and the thickness of each layer 102, 104 are determined from the spectral attributes acquired from a spectroscopic analysis of a characteristic of the substance using a conventional spectroscopic instrument. The spectrum of interest of a given characteristic of a substance typically includes any number of different wavelengths. It should be understood that the exemplary ICE 100 in FIG. 1 does not in fact represent any particular characteristic of a given substance, but is provided for purposes of illustration only. Consequently, the number of layers 102, 104 and their relative thicknesses, as shown in FIG. 1, bear no correlation to any particular characteristic of a given substance. Nor are the layers 102, 104 and their relative thicknesses necessarily drawn to scale, and therefore should not be considered limiting of the present disclosure. Moreover, those skilled in the art will readily recognize that the materials that make up each layer 102, 104 (i.e., Si and $SiO_2$) may vary, depending on the application, cost of materials, and/or applicability of the material to the substance.

In some embodiments, the material of each layer 102, 104 can be doped or two or more materials can be combined in a manner to achieve the desired optical characteristic. In addition to solids, the exemplary ICE 100 may also contain liquids and/or gases, optionally in combination with solids, in order to produce a desired optical characteristic. In the case of gases and liquids, the ICE 100 can contain a corresponding vessel (not shown), which houses the gases or liquids. Exemplary variations of the ICE 100 may also include holographic optical elements, gratings, piezoelectric, light pipe, digital light pipe (DLP), and/or acousto-optic elements, for example, that can create transmission, reflection, and/or absorptive properties of interest.

The multiple layers 102, 104 exhibit different refractive indices. By properly selecting the materials of the layers 102, 104 and their relative thickness and spacing, the ICE 100 may be configured to selectively pass/reflect/refract predetermined fractions of electromagnetic radiation at different wavelengths. Each wavelength is given a predetermined weighting or loading factor. The thickness and spacing of the layers 102, 104 may be determined using a variety of approximation methods from the spectrograph of the characteristic or analyte of interest. These methods may include inverse Fourier transform (IFT) of the optical transmission spectrum and structuring the ICE 100 as the physical representation of the IFT. The approximations convert the IFT into a structure based on known materials with constant refractive indices.

Further information regarding the structures and design of exemplary integrated computational elements (also referred to as multivariate optical elements) is provided in *Applied Optics*, Vol. 35, pp. 5484-5492 (1996) and Vol. 129, pp. 2876-2893, which is hereby incorporated by reference.

The weightings that the layers 102, 104 of the ICE 100 apply at each wavelength are set to the regression weightings described with respect to a known equation, or data, or spectral signature. Briefly, the ICE 100 may be configured to perform the dot product of the input light beam into the ICE 100 and a desired loaded regression vector represented by each layer 102, 104 for each wavelength. As a result, the output light intensity of the ICE 100 is related to the characteristic or analyte of interest. Further details regarding how the exemplary ICE 100 is able to distinguish and process electromagnetic radiation related to the characteristic or analyte of interest are described in U.S. Pat. Nos. 6,198,531; 6,529,276; and 7,920,258, previously incorporated herein by reference.

Figure 2:
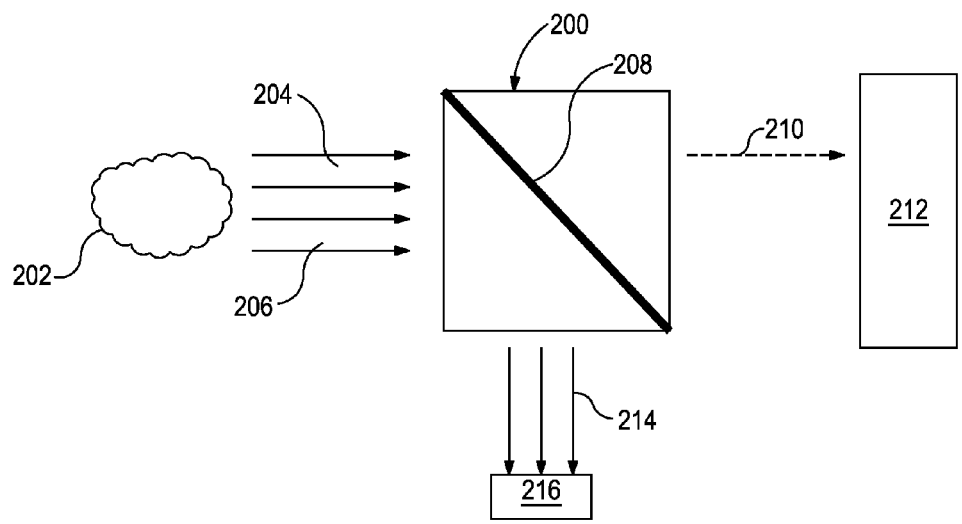
FIG. 2 illustrates a block diagram non-mechanistically illustrating how an optical computing device distinguishes electromagnetic radiation related to a characteristic of interest from other electromagnetic radiation, according to one or more embodiments.

Referring now to FIG. 2, illustrated is a block diagram that non-mechanistically illustrates how an optical computing device 200 is able to distinguish electromagnetic radiation related to a characteristic of a substance from other electromagnetic radiation. As shown in FIG. 2, after being illuminated with incident electromagnetic radiation, a fluid 202 containing a characteristic of interest or a substance produces an output of electromagnetic radiation (e.g., sample-interacted light), some of which is electromagnetic radiation 204 corresponding to the characteristic of interest and some of which is background electromagnetic radiation 206 corresponding to other components or characteristics of the fluid 202.

Although not specifically shown, one or more spectral elements may be employed in the device 200 in order to restrict the optical wavelengths and/or bandwidths of the system and thereby eliminate unwanted electromagnetic radiation existing in wavelength regions that have no importance. Such spectral elements can be located anywhere along the optical train, but are typically employed directly after the light source, which provides the initial electromagnetic radiation. Various configurations and applications of spectral elements in optical computing devices may be found in commonly owned U.S. Pat. Nos. 6,198,531; 6,529,276; 7,123,844; 7,834,999; 7,911,605, 7,920,258, 8,049,881, and U.S. patent application Ser. No. 12/094,460 (U.S. Pat. App. Pub. No. 2009/0219538); Ser. No. 12/094,465 (U.S. Pat. App. Pub. No. 2009/0219539); and Ser. No. 13/456,467, incorporated herein by reference, as indicated above.

The beams of electromagnetic radiation 204, 206 impinge upon the optical computing device 200, which contains an exemplary ICE 208 therein. In the illustrated embodiment, the ICE 208 may be configured to produce optically interacted light, for example, transmitted optically interacted light 210 and reflected optically interacted light 214. In operation, the ICE 208 may be configured to distinguish the electromagnetic radiation 204 from the background electromagnetic radiation 206.

The transmitted optically interacted light 210, which may be related to the characteristic or analyte of interest of the fluid 202, may be conveyed to a detector 212 for analysis and quantification. In some embodiments, the detector 212 is configured to produce an output signal in the form of a voltage that corresponds to the particular characteristic of the fluid 202. In at least one embodiment, the signal produced by the detector 212 and the concentration of the characteristic of the fluid 202 may be directly proportional. In other embodiments, the relationship may be a polynomial function, an exponential function, and/or a logarithmic function. The reflected optically interacted light 214, which may be related to the characteristic and other components of the fluid 202, can be directed away from detector 212. In alternative configurations, the ICE 208 may be configured such that the reflected optically interacted light 214 can be related to the analyte of interest, and the transmitted optically interacted light 210 can be related to other components of the fluid 202.

In some embodiments, a second detector 216 can be present and arranged to detect the reflected optically interacted light 214. In other embodiments, the second detector 216 may be arranged to detect the electromagnetic radiation 204, 206 derived from the fluid 202 or electromagnetic radiation directed toward or before the fluid 202. Without limitation, the second detector 216 may be used to detect radiating deviations stemming from an electromagnetic radiation source (not shown), which provides the electromagnetic radiation (i.e., light) to the device 200. For example, radiating deviations can include such things as, but not limited to, intensity fluctuations in the electromagnetic radiation, interferent fluctuations (e.g., dust or other interferents passing in front of the electromagnetic radiation source), coatings on windows included with the optical computing device 200, combinations thereof, or the like. In some embodiments, a beam splitter (not shown) can be employed to split the electromagnetic radiation 204, 206, and the transmitted or reflected electromagnetic radiation can then be directed to one or more ICE 208. That is, in such embodiments, the ICE 208 does not function as a type of beam splitter, as depicted in FIG. 2, and the transmitted or reflected electromagnetic radiation simply passes through the ICE 208, being computationally processed therein, before travelling to the detector 212.

The characteristic(s) of the fluid 202 being analyzed using the optical computing device 200 can be further processed computationally to provide additional characterization information about the fluid 202. In some embodiments, the identification and concentration of each analyte in the fluid 202 can be used to predict certain physical characteristics of the fluid 202. For example, the bulk characteristics of a fluid 202 can be estimated by using a combination of the properties conferred to the fluid 202 by each analyte.

In some embodiments, the concentration of each analyte or the magnitude of each characteristic determined using the optical computing device 200 can be fed into an algorithm operating under computer control. The algorithm may be configured to make predictions on how the characteristics of the fluid 202 change if the concentrations of the analytes are changed relative to one another. In some embodiments, the algorithm can produce an output that is readable by an operator who can manually take appropriate action, if needed, based upon the output. In some embodiments, the algorithm can take proactive process control by automatically adjusting flow parameters of a flow path, such as reducing fluid flow rate or pressure within the flow path, in order to manipulate the characteristics of the fluid.

The algorithm can be part of an artificial neural network configured to use the concentration of each detected analyte in order to evaluate the overall characteristic(s) of the fluid 202 and predict how to modify the fluid 202 or a fluid flow in order to alter the properties of the fluid or a related system in a desired way. Illustrative but non-limiting artificial neural networks are described in commonly owned U.S. patent application Ser. No. 11/986,763 (U.S. Patent Application Publication 2009/0182693), which is incorporated herein by reference. It is to be recognized that an artificial neural network can be trained using samples of substances having known concentrations, compositions, and/or properties, and thereby generating a virtual library. As the virtual library available to the artificial neural network becomes larger, the neural network can become more capable of accurately predicting the characteristics of a substance having any number of analytes present therein. Furthermore, with sufficient training, the artificial neural network can more accurately predict the characteristics of the substance, even in the presence of unknown analytes.

It is recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

In some embodiments, the data collected using the optical computing devices can be archived along with data associated with operational parameters being logged at a job site. Evaluation of job performance can then be assessed and improved for future operations or such information can be used to design subsequent operations. In addition, the data and information can be communicated (wired or wirelessly) to a remote location by a communication system (e.g., satellite communication or wide area network communication) for further analysis. The communication system can also allow remote monitoring and operation of a process to take place. Automated control with a long-range communication system can further facilitate the performance of remote job operations. In particular, an artificial neural network can be used in some embodiments to facilitate the performance of remote job operations. That is, remote job operations can be conducted automatically in some embodiments. In other embodiments, however, remote job operations can occur under direct operator control, where the operator is not at the job site.

Figure 3:
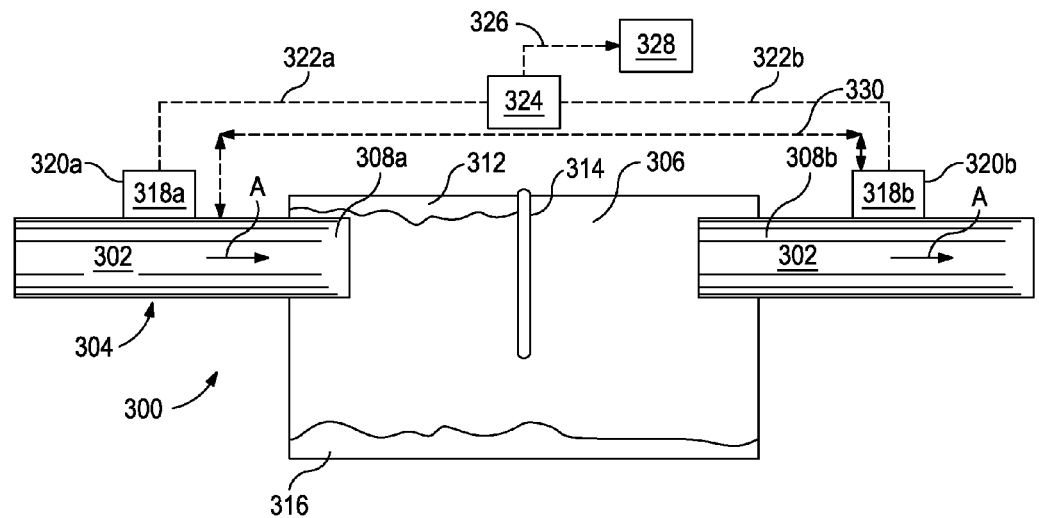
FIG. 3 illustrates an exemplary system for monitoring a fluid, according to one or more embodiments.

Referring now to FIG. 3, illustrated is an exemplary system 300 for monitoring a fluid 302, according to one or more embodiments. In the illustrated embodiment, the fluid 302 may be contained or otherwise flowing within a flow path 304. The flow path 304 may be a flow line or a pipeline and the fluid 302 present therein may be flowing in the general direction indicated by the arrows A (i.e., from an upstream location to a downstream location). As will be appreciated, however, the flow path 304 may be any other type of flow path, as generally described or otherwise defined herein.

In at least one embodiment, the flow path 304 may form part of an oil/gas pipeline and may be arranged near a wellhead or form part of a plurality of subsea and/or above-ground interconnecting flow lines or pipelines that interconnect various subterranean hydrocarbon reservoirs with one or more receiving/gathering platforms or process facilities. In some embodiments, all or a portion of the depicted flow path 304 may be employed downhole. In other embodiments, all or a portion of the depicted flow path 304 may be employed above-ground at or near a surface facility, for example. As such, portions of the flow path 304 may be arranged substantially vertical, substantially horizontal, or any directional configuration therebetween, without departing from the scope of the disclosure.

As illustrated, the flow path 304 may include or otherwise be fluidly coupled to a fluid separator 306. In some embodiments, the fluid separator 306 may form an integral part of the flow path 304, where the inlet and discharge conduits 308a,b provide transition locations or points between the flow lines of the flow path 304 and the fluid separator 306. The fluid separator 306 may be configured to receive the fluid 302 via an inlet conduit 308a and discharge the fluid 302 via at least one discharge conduit 308b after one or more constituent components is separated therefrom. Accordingly, in some embodiments, the fluid 302 contained or otherwise flowing through the discharge conduit 308b may be characterized or otherwise referred to as a "separated fluid." While only one inlet conduit 308a and only one discharge conduit 308b are depicted in FIG. 3, it will be appreciated that more than one inlet conduit 308a and one discharge conduit 308b may be employed without departing from the scope of the disclosure.

The fluid separator 306 may be any type of separator known to those skilled in the art and used to separate one or more components in the fluid 302 from one or more other components in the fluid 302. In oil and gas applications, for example, the fluid separator 306 may be any type of separator used to separate wellbore production fluids into their constituent components of, for example, oil, gas, water, precipitates, impurities, condensates (e.g., BTEX compounds), multiphase fluids, combinations thereof, and the like. Suitable separators include separators that operate on the principle of density separation or separators that operate on the principle of centrifuge separation. In operation, the higher density material or substance (e.g., water) is separated from the lower density material or substance (e.g., gas, oil, impurities, etc.) via differential settling or centrifuging, as known in the art. In some embodiments, various materials, chemicals, or substances, as known in the art, may be added to the fluid 302 to help facilitate a more efficient separation process. Other suitable separators 306 may include, but are not limited to, oil and gas separators, stage separators, trap separators, knockout vessels (knockout drum, knockout trap, water knockout, or liquid knockout), flash chamber separators (flash vessel or flash trap), expansion separator or expansion vessel, scrubbers (gas scrubber), corrugated plate receptors, filters (gas filter), cyclone technology (gas/solid separation, hydrocyclones for liquid phase separation), and flocculent assisted dissolved air and induced air flotation (DAF, IAF for solid and oil separation for oily waste treatment). Suitable separators 306 may have three general configurations: vertical, horizontal, and spherical.

As depicted, and in the context of the oil and gas industry, the fluid separator 306 may operate to separate oil/gas 312 from the fluid 302 and a foam breaker or divider 314 may be arranged within the fluid separator 306 in order to isolate the separated oil/gas 312 from any remaining components of the fluid 302 and to otherwise facilitate removal of the oil/gas 312 from the fluid separator 306. The fluid separator 306 may also operate to separate any precipitates 316 from the fluid 302, which may, for example, settle or otherwise coalesce near the bottom of the fluid separator 306. Once substantially separated from the oil/gas 312 and/or the precipitates 316, the fluid 302 exits the fluid separator 306 via the discharge conduit 308b. As will be appreciated by those skilled in the art, the illustrated fluid separator 306 is described merely by example in order to supplement understanding of the exemplary systems and methods described herein. Accordingly, in no way should the described components or separation processes discussed herein as related to the fluid separator 306 be considered as limiting the scope of the present disclosure. Indeed, those skilled in the art will readily recognize several variations or configurations of the fluid separator 306 that may be employed without departing from the scope of the disclosure.

The system 300 may further include at least a first optical computing device 318a and a second optical computing device 318b. The optical computing devices 318a,b may be somewhat similar to the optical computing device 200 of FIG. 2, and therefore may be best understood with reference thereto. As illustrated, the first and second optical computing devices 318a,b may each be associated with the flow path 304 at independent and distinct monitoring locations along the flow path 304. Specifically, the first optical computing device 318a may be located at, near (e.g., adjacent to or in proximity of), or before the inlet conduit 308a, and the second optical computing device 318b may be located at, near (e.g., adjacent to or in proximity of), or after the discharge conduit 308b. The optical computing devices 318a,b may be useful in determining a particular characteristic of the fluid 302 within the flow path 304, such as determining how the concentration of a substance present within the fluid 302 changes after passing through the fluid separator 306. It should be noted that, while only two optical computing devices 318a,b are shown in FIG. 3, it will be appreciated that the system 300 may employ more than two optical computing devices within the flow path 304, without departing from the scope of the disclosure.

Each device 318a,b may be housed within an individual casing or housing coupled or otherwise attached to the flow path 304 at its respective location. As illustrated, for example, the first device 318a may be housed within a first housing 320a and the second device 318b may be housed within a second housing 320b. In some embodiments, the first and second housings 320a,b may be mechanically coupled to the flow path 304 using, for example, mechanical fasteners, brazing or welding techniques, adhesives, magnets, combinations thereof or the like. Each housing 320a,b may be configured to substantially protect the internal components of the respective devices 318a,b from damage or contamination from the external environment. Moreover, each housing 320a,b may be designed so as to withstand the pressures that may be experienced within the flow path 304 and thereby provide a fluid tight seal between the flow path 304 and the respective housing 320a,b.

As will be described in more detail below, each device 318a,b may be configured to produce an output signal in real-time or near real-time in the form of a voltage (or current) that corresponds to particular characteristic of interest in the fluid 302. For example, the first device 318a may generate a first output signal 322a and the second device 318b may generate a second output signal 322b. In some embodiments, the output signal 322a,b from each device 318a,b may be conveyed to or otherwise received by a signal processor 324 communicably coupled to each device 318a,b. The signal processor 324 may be a computer including a non-transitory machine-readable medium, and may employ an algorithm configured to calculate or otherwise determine the differences between the two output signals 322a,b. For example, the first output signal 322a may be indicative of the concentration of a substance and/or the magnitude of the characteristic of interest in the fluid 302 at the location of the first device 318a along the flow path 304, and the second output signal 322b may be indicative of the concentration of the substance and/or the magnitude of the characteristic of interest in the fluid 302 at the location of the second device 318b along the flow path 304. Accordingly, in at least one embodiment, the signal processor 324 may be configured to determine how the concentration of the substance and/or the magnitude of the characteristic of interest in the fluid 302 has changed by passing through the fluid separator 306.

In real-time or near real-time, the signal processor 324 may be configured to provide a resulting output signal 326 which may be conveyed, either wired or wirelessly, to a user for consideration. In at least one embodiment, as briefly mentioned above, the resulting output signal 326 may correspond to a measured difference in the substance and/or the magnitude of the characteristic of interest in the fluid 302 between the first and second optical computing devices 318a,b. For example, in one or more embodiments, the first and second output signals 322a,b may be indicative of a concentration of a substance, such as a hydrocarbon or other common production fluid component, flowing with the fluid 302. The first optical computing device 318a may be configured to determine and report the concentration of the substance at, near, or before the inlet conduit 308a, and the second optical computing device 318b may be configured to determine and report the concentration of the substance at, near, or after the discharge conduit 308b. By calculating the difference between the first and second output signals 322a,b, the signal processor 324 may be able to determine how efficiently the fluid separator 306 operates.

In other embodiments, the first and second output signals 322a,b may be indicative of a characteristic of interest of the fluid 302 itself, such as any chemical, mechanical, or physical property of the fluid 302. In at least one embodiment, the characteristic of interest may refer to an impurity content of the fluid 302, such as the presence of salts, precipitates, water (i.e., in the case of hydrocarbon separation) and hydrocarbons (i.e., in the case of water separation), particles, tags (e.g., chemical or physical), metals, organic compounds and volatile organic compounds, additives and treatments, polymers, biological organisms (e.g., bacteria, viruses, microorganisms, etc.) drugs and medicines, poisons, or other components of interest. The first optical computing device 318a may be configured to determine and report the concentration of the impurity content at, near, or before the inlet conduit 308a, and the second optical computing device 318b may be configured to determine and report the concentration of the impurity content at, near, or before the discharge conduit 308b. Accurately calculating and reporting the impurity content of the fluid 302 in real-time or near real-time may prove advantageous in quality control applications where the fluid 302 exiting the fluid separator 306 must, for example, adhere to strict environmental rules and regulations. For example, state and national regulations often determine that oil in waste water concentrations are less than 5 ppm for discharge into inland water ways and 20-30 ppm in the open ocean. The system 300, and its variations, may be used to ensure that the concentration of oil in waste water do not exceed these predetermined limits.

In other embodiments, the first and second output signals 322a,b may be indicative of fluid compositions and fluid phases. For example, the first and second output signals 322a,b may be indicative of characteristics such as density, specific gravity, pH, total dissolved solids, sand or particulates, combinations thereof, and the like. In yet other embodiments, the first and second output signals 322a,b may be indicative of the concentration or content of one or more treatment chemicals added to the fluid 302. In many circumstances, for example, separation operations may be assisted by the use of one or more treatment chemicals, such as emulsion breakers, de-foaming agents, digester organisms, coalescing agents, and flocculants. The relative concentrations of such treatment chemicals can be monitored and measured using the system 300, and its variations.

In yet other embodiments, the resulting output signal 326 may be recognized by the signal processor 324 as being within or without a predetermined or preprogrammed range of suitable operation for the flow path 304. For example, the first and second output signals 322a,b may report general fluid conditions in the flow path 304 on respective sides of the fluid separator 306 and may be configured to warn a user if the level of the oil (or other substance to be separated using the fluid separator 306) has surpassed a predetermined level. In some aspects, the first output signal 322a derived from the first optical computing device 318a may be configured to provide an early warning of a potential overload of the fluid separator 306. Likewise, the second output signal 322b derived from the second optical computing device 318b may be configured to provide an alert that an impurity, such as oil or another hydrocarbon, is exiting the fluid separator 306 via the discharge conduit 308b.

In at least one embodiment, the system 300 may be or otherwise include an automated control system 328 configured to autonomously react to resulting output signals 326 that are within or without predetermined or preprogrammed ranges of suitable operation for the flow path 304. For example, if the resulting output signal 326 exceeds the predetermined or preprogrammed range of operation, the automated control system 328 may be configured to alert the user so appropriate corrective action may be taken, or otherwise autonomously undertake the appropriate corrective action such that the resulting output signal 326 returns to a value that falls within the predetermined or preprogrammed range of operation. Such corrective actions may entail adjusting the parameters or conditions of the fluid 302, such as by manipulating fluid flow, pressure, temperature, flow path direction (e.g., changing the route of the fluid flow), adding treatments and/or other additives (all types), increasing or decreasing the speed of rotation of disc stage centrifuges, adjusting electrical or magnetic fields, adjusting light exposure and/or air flow, combinations thereof, and the like.

Still referring to FIG. 3, in other embodiments, the first optical computing device 318a may be omitted from the system 300 and instead an optical light pipe 330 may be included to facilitate the monitoring and/or detection of the fluid 302 at or near the inlet conduit 308a. The optical light pipe 330 may be a fiber optic lead, probe, or conduit used for the transmission of electromagnetic radiation to/from the second optical computing device 318b. Specifically, the optical light pipe may communicably couple the second optical computing device 318b to the fluid at or near the inlet conduit 308a. For example, the optical light pipe 330 may be configured to convey electromagnetic radiation from the second optical computing device 318 to the fluid 302 for the purpose of determining the particular characteristic of interest. The optical light pipe 330 may also be configured to convey optically interacted radiation from the fluid 302 to the second optical computing device 318b.

In exemplary operation, the second optical computing device 318b may receives optically interacted radiation from the fluid 302 at or near the inlet conduit 308a via the optical light pipe 330 and also at or near the discharge conduit 308b via the process described above. In some embodiments, a detector (not shown, but described below in FIG. 4 as detector 414) arranged within the second optical computing device 316 may be configured to time multiplex the dual beams of optically interacted light from the fluid 302. For example, the optically interacted radiation received via the optical light pipe 330 may be directed to or otherwise received by the second optical computing device 318b at a first time T1, and the optically interacted radiation derived at or near the discharge conduit 308b may be directed to or otherwise received by the second optical computing device 318b at a second time T2, where the first and second times T1, T2 are distinct time periods that do not spatially overlap.

Consequently, the detector receives at least two distinct beams of optically interacted light and is able to convey corresponding second output signals 322b for the respective beams to the signal processor for processing. The first beam of optically interacted light may indicate the concentration of a substance and/or the magnitude of the characteristic of interest in the fluid 302 at or near the inlet conduit 318a, while the second beam of optically interacted light may indicate the concentration of a substance and/or the magnitude at or near the discharge conduit 318b. By calculating the difference between the corresponding second output signals 322b, the signal processor 324 may be able to determine how efficiently the fluid separator 306 operates or determine how the concentration of the substance and/or the magnitude of the characteristic of interest in the fluid 302 has changed by passing through the fluid separator 306.

Figure 4:
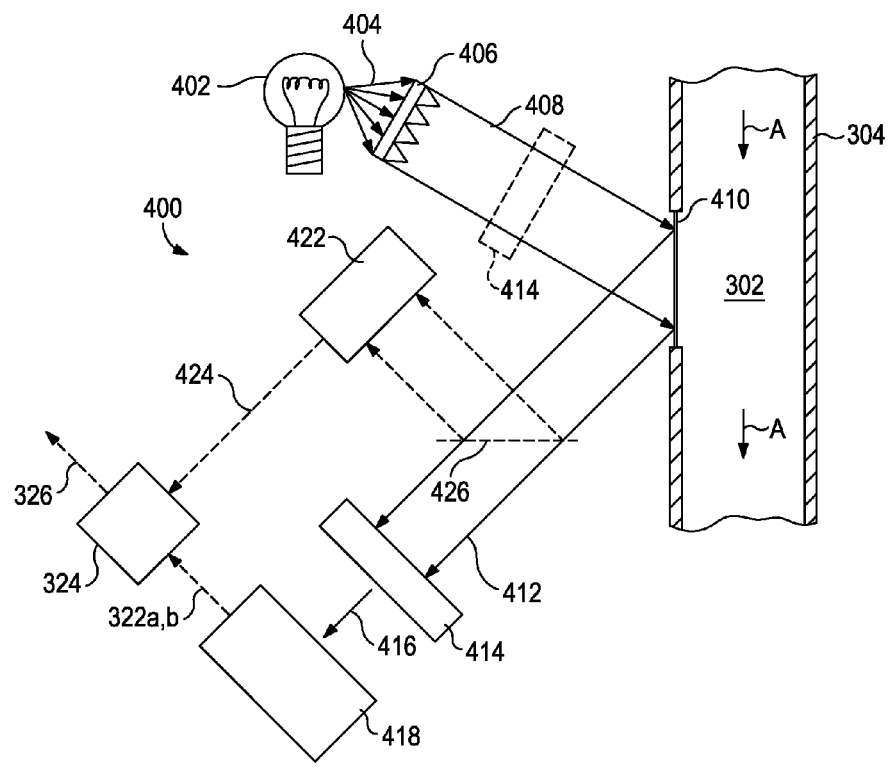
FIG. 4 illustrates an exemplary optical computing device, according to one or more embodiments.

Referring now to FIG. 4, with continued reference to FIG. 3, illustrated is a schematic view of an exemplary optical computing device 400, which may represent a more detailed view of the first and/or second optical computing devices 318a,b, according to one or more embodiments. As illustrated, the optical computing device 400 may be coupled or otherwise attached to the flow path 304 in order to monitor the fluid 302 before and/or after the fluid separator 306 (FIG. 3). The optical computing device 400 may include an electromagnetic radiation source 402 configured to emit or otherwise generate electromagnetic radiation 404. The electromagnetic radiation source 402 may be any device capable of emitting or generating electromagnetic radiation, as defined herein. For example, the electromagnetic radiation source 402 may be a light bulb, a light emitting device (LED), a laser, a blackbody, a photonic crystal, an X-Ray source, combinations thereof, or the like.

In some embodiments, a lens 406 may be configured to collect or otherwise receive the electromagnetic radiation 404 and direct a beam 408 of electromagnetic radiation 404 toward the fluid 302. The lens 406 may be any type of optical device configured to transmit or otherwise convey the electromagnetic radiation 404 as desired. For example, the lens 406 may be a normal lens, a Fresnel lens, a diffractive optical element, a holographic graphical element, a mirror (e.g., a focusing mirror), a type of collimator, or any other electromagnetic radiation transmitting device known to those skilled in art. In other embodiments, the lens 406 may be omitted from the optical computing device 400 and the electromagnetic radiation 404 may instead be directed toward the fluid 302 directly from the electromagnetic radiation source 402.

In one or more embodiments, the optical computing device 400 may also include a sampling window 410 arranged adjacent to or otherwise in contact with the fluid 302 for detection purposes. The sampling window 410 may be made from a variety of transparent, rigid or semi-rigid materials that are configured to allow transmission of the electromagnetic radiation 404 therethrough. For example, the sampling window 410 may be made of, but is not limited to, glasses, plastics, semi-conductors, crystalline materials, polycrystalline materials, hot or cold-pressed powders, combinations thereof, or the like. In order to remove ghosting or other common imaging issues that may result from reflectance on the sampling window 410, the optical computing device 400 may employ one or more internal reflectance elements (IRE), such as those described in co-owned U.S. Pat. No. 7,697,141, and/or one or more imaging systems, such as those described in co-owned U.S. patent application Ser. No. 13/456,467, the contents of each hereby being incorporated by reference.

After passing through the sampling window 410, the electromagnetic radiation 404 impinges upon and optically interacts with the fluid 302. As a result, optically interacted radiation 412 is generated by and reflected from the fluid 302. Those skilled in the art, however, will readily recognize that alternative variations of the optical computing device 400 may allow the optically interacted radiation 412 to be generated by being transmitted, scattered, diffracted, absorbed, emitted, or re-radiated by and/or from the fluid 302, without departing from the scope of the disclosure.

The optically interacted radiation 412 generated by the optical interaction with the fluid 302 may be directed to or otherwise be received by an ICE 414 arranged within the optical computing device 400. The ICE 414 may be a spectral component substantially similar to the ICE 100 described above with reference to FIG. 1. Accordingly, in operation the ICE 414 may be configured to receive the optically interacted radiation 412 and produce modified electromagnetic radiation 416 corresponding to a particular characteristic of interest of the fluid 302. In particular, the modified electromagnetic radiation 416 is electromagnetic radiation that has optically interacted with the ICE 414, whereby an approximate mimicking of the regression vector corresponding to the characteristic of interest in the fluid 302 is obtained.

It should be noted that, while FIG. 4 depicts the ICE 414 as receiving electromagnetic radiation as reflected from the fluid 302, the ICE 414 may be arranged at any point along the optical train of the optical computing device 400, without departing from the scope of the disclosure. For example, in one or more embodiments, the ICE 414 (as shown in dashed) may be arranged within the optical train prior to the sampling window 410 and equally obtain substantially the same results. In other embodiments, the sampling window 410 may serve a dual purpose as both a transmission window and the ICE 414 (i.e., a spectral component). In yet other embodiments, the ICE 414 may generate the modified electromagnetic radiation 416 through reflection, instead of transmission therethrough.

Moreover, while only one ICE 414 is shown in the optical computing device 400, embodiments are contemplated herein which include the use of at least two ICE components in the optical computing device 400 configured to cooperatively determine the characteristic of interest in the fluid 302. For example, two or more ICE may be arranged in series or parallel within the optical computing device 400 and configured to receive the optically interacted radiation 412 and thereby enhance sensitivities and detector limits of the optical computing device 400. In other embodiments, two or more ICE may be arranged on a movable assembly, such as a rotating disc or an oscillating linear array, which moves such that the individual ICE components are able to be exposed to or otherwise optically interact with electromagnetic radiation for a distinct brief period of time. The two or more ICE components in any of these embodiments may be configured to be either associated or disassociated with the characteristic of interest in the fluid 302. In other embodiments, the two or more ICE may be configured to be positively or negatively correlated with the characteristic of interest in the fluid 302. Additional discussion of these optional embodiments employing two or more ICE components can be found in co-pending U.S. patent application Ser. Nos. 13/456,264, 13/456,405, 13/456,302, and 13/456,327, the contents of which are hereby incorporated by reference in their entireties.

In some embodiments, it may be desirable to monitor more than one characteristic of interest at a time using the optical computing device 400. In such embodiments, various configurations for multiple ICE components can be used, where each ICE component is configured to detect a particular and/or distinct characteristic of interest. In some embodiments, the characteristic can be analyzed sequentially using multiple ICE components that are provided a single beam of electromagnetic radiation as reflected from or transmitted through the fluid 302. In some embodiments, as briefly mentioned above, multiple ICE components can be arranged on a rotating disc, where the individual ICE components are only exposed to the beam of electromagnetic radiation for a short time. Advantages of this approach can include the ability to analyze multiple characteristics or analytes within the fluid 302 using a single optical computing device and the opportunity to assay additional analytes simply by adding additional ICE components to the rotating disc. In various embodiments, the rotating disc can be turned at a frequency of about 10 RPM to about 30,000 RPM such that each analyte in the fluid 302 is measured rapidly. In some embodiments, these values can be averaged over an appropriate time domain (e.g., about 1 millisecond to about 1 hour) to more accurately determine the characteristics of the fluid 302.

In other embodiments, multiple optical computing devices can be placed at a single location along the flow path 304, either at the inlet conduit 308a or the discharge conduit 308b of the fluid separator 306, and each optical computing device may contain a unique ICE that is configured to detect a particular characteristic of interest in the fluid 302. In such embodiments, a beam splitter can divert a portion of the electromagnetic radiation being reflected by, emitted from, or transmitted through the fluid 302 and into each optical computing device. Each optical computing device, in turn, can be coupled to a corresponding detector or detector array that is configured to detect and analyze an output of electromagnetic radiation from the respective optical computing device. Parallel configurations of optical computing devices can be particularly beneficial for applications that require low power inputs and/or no moving parts.

Those skilled in the art will appreciate that any of the foregoing configurations can further be used in combination with a series configuration in any of the present embodiments. For example, two optical computing devices having a rotating disc with a plurality of ICE components arranged thereon can be placed in series for performing an analysis at a single location along the length of the flow path 304. Likewise, multiple detection stations, each containing optical computing devices in parallel, can be placed in series for performing a similar analysis.

The modified electromagnetic radiation 416 generated by the ICE 414 may subsequently be conveyed to a detector 418 for quantification of the signal. The detector 418 may be any device capable of detecting electromagnetic radiation, and may be generally characterized as an optical transducer. In some embodiments, the detector 418 may be, but is not limited to, a thermal detector such as a thermopile or photoacoustic detector, a semiconductor detector, a piezo-electric detector, a charge coupled device (CCD) detector, a video or array detector, a split detector, a photon detector (such as a photomultiplier tube), photodiodes, combinations thereof, or the like, or other detectors known to those skilled in the art.

The detector 418 may be configured to produce an output signal, such as one or the first and second output signals 322a and 322b, as generally discussed above with reference to FIG. 3. The output signal 322a,b may be generated in real-time or near real-time and may be conveyed in the form of a voltage (or current) that corresponds to the particular characteristic of interest in the fluid 302. The voltage returned by the detector 418 is essentially the dot product of the optical interaction of the optically interacted radiation 412 with the respective ICE 414 as a function of the concentration of the characteristic of interest of the fluid 302. As such, the output signal 322a,b produced by the detector 418 and the concentration of the characteristic of interest in the fluid 302 may be related, for example, directly proportional. In other embodiments, however, the relationship may correspond to a polynomial function, an exponential function, a logarithmic function, and/or a combination thereof.

In some embodiments, the optical computing device 400 may include a second detector 422, which may be similar to the first detector 418 in that it may be any device capable of detecting electromagnetic radiation. Similar to the second detector 216 of FIG. 2, the second detector 422 of FIG. 4 may be used to detect radiating deviations stemming from the electromagnetic radiation source 402. Undesirable radiating deviations can occur in the intensity of the electromagnetic radiation 404 due to a wide variety of reasons and potentially causing various negative effects on the optical computing device 400. These negative effects can be particularly detrimental for measurements taken over a period of time. In some embodiments, radiating deviations can occur as a result of a build-up of film or material on the sampling window 410 which has the effect of reducing the amount and quality of light ultimately reaching the first detector 418. Without proper compensation, such radiating deviations could result in false readings and the output signal 322a,b would no longer be primarily or accurately related to the characteristic of interest.

To compensate for these types of undesirable effects, the second detector 422 may be configured to generate a compensating signal 424 generally indicative of the radiating deviations of the electromagnetic radiation source 402, and thereby normalize the output signal 322a,b generated by the first detector 418. As illustrated, the second detector 422 may be configured to receive a portion of the optically interacted radiation 412 via a beamsplitter 426 in order to detect the radiating deviations. In other embodiments, however, the second detector 422 may be arranged to receive electromagnetic radiation from any portion of the optical train in the optical computing device 400 in order to detect the radiating deviations, without departing from the scope of the disclosure.

In some applications, the output signal 322a,b and the compensating signal 424 may be conveyed to (either jointly or separately) or otherwise received by a signal processor 324. The signal processor 324 may be configured to computationally combine the compensating signal 424 with the output signal 322a,b in order to normalize the output signal 322a,b in view of any radiating deviations detected by the second detector 422. In some embodiments, computationally combining the output and compensating signals 320, 328 may entail computing a ratio of the two signals 322a,b, 424. For example, the concentration or magnitude of each characteristic determined using the optical computing device 400 can be fed into an algorithm run by the signal processor 324. The algorithm may be configured to make predictions on how the characteristics of the fluid 302 change if the concentrations of the analytes are changed relative to one another.

Figure 5:
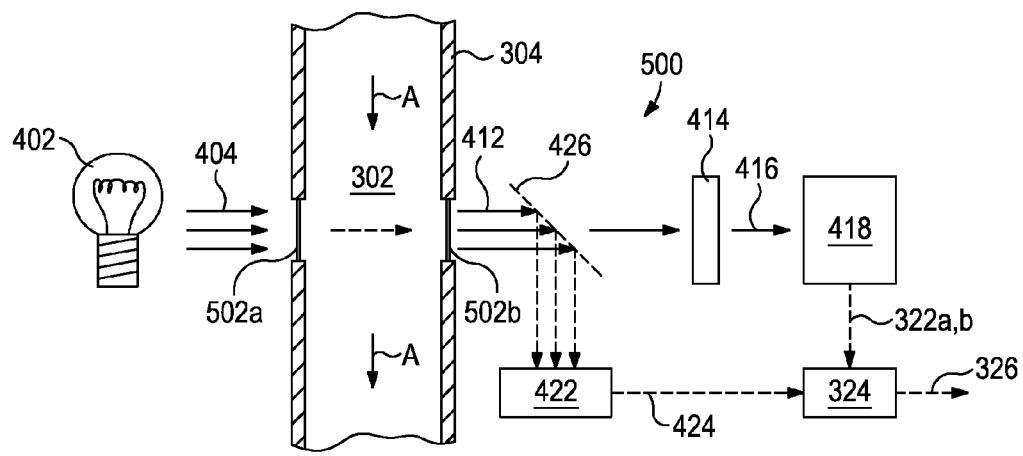
FIG. 5 illustrates another exemplary optical computing device, according to one or more embodiments.

Referring now to FIG. 5, with continued reference to FIGS. 3 and 4, illustrated is a schematic view of another exemplary optical computing device 500, according to one or more embodiments. As with the optical computing device 400 of FIG. 4, the optical computing device 500 of FIG. 5 may also represent a more detailed view of the first and/or second optical computing devices 318a,b, albeit an alternative to the optical computing device 400. Accordingly, the optical computing device 500 may be similar in some respects to the optical computing device 400 of FIG. 4, and therefore may be best understood with reference thereto where like numerals will indicate like elements that will not be described again. The optical computing device 500 may again be configured to determine the concentration of a characteristic of interest in the fluid 302 as contained within the flow path 304. Unlike the optical computing device 400 in FIG. 4, however, the optical computing device 500 in FIG. 5 may be configured to transmit the electromagnetic radiation through the fluid 302 via a first sampling window 502a and a second sampling window 502b arranged radially-opposite the first sampling window 502a. The first and second sampling windows 502a,b may be similar to the sampling window 410 described above in FIG. 4.

As the electromagnetic radiation 404 passes through the fluid 302 via the first and second sampling windows 502a,b, it optically interacts with the fluid 302. Optically interacted radiation 412 is subsequently directed to or otherwise received by the ICE 414 as arranged within the optical computing device 500. It is again noted that, while FIG. 5 depicts the ICE 414 as receiving the optically interacted radiation 412 as transmitted through the sampling windows 502a,b, the ICE 414 may equally be arranged at any point along the optical train of the optical computing device 500, without departing from the scope of the disclosure. For example, in one or more embodiments, the ICE 414 may be arranged within the optical train prior to the first sampling window 502a and equally obtain substantially the same results. In other embodiments, one or each of the first or second sampling windows 502a,b may serve a dual purpose as both a transmission window and the ICE 414 (i.e., a spectral component). In yet other embodiments, the ICE 414 may generate the modified electromagnetic radiation 416 through reflection, instead of transmission therethrough. Moreover, as with the system 300 of FIG. 3, embodiments are contemplated herein which include the use of at least two ICE components in the optical computing device 500 configured to cooperatively determine the characteristic of interest in the fluid 302.

The modified electromagnetic radiation 416 generated by the ICE 414 is subsequently conveyed to the detector 418 for quantification of the signal and generation of an output signal (i.e., output signals 322a or 322b) which corresponds to the particular characteristic of interest in the fluid 302. The optical computing device 500 may also include the second detector 422 for detecting radiating deviations stemming from the electromagnetic radiation source 402. As illustrated, the second detector 422 may be configured to receive a portion of the optically interacted radiation 412 via the beamsplitter 426 in order to detect the radiating deviations. In other embodiments, however, the second detector 422 may be arranged to receive electromagnetic radiation from any portion of the optical train in the optical computing device 500 in order to detect the radiating deviations, without departing from the scope of the disclosure. The output signal 322a,b and the compensating signal 424 may then be conveyed to (either jointly or separately) or otherwise received by the signal processor 324 which may computationally combine the two signals 322a,b and 424 and provide in real-time or near real-time the resulting output signal 326 corresponding to the concentration of the characteristic of interest in the fluid 302.

Still referring to FIG. 5, with additional reference to FIG. 4, those skilled in the art will readily recognize that, in one or more embodiments, electromagnetic radiation may be derived from the fluid 302 itself, and otherwise derived independent of the electromagnetic radiation source 402. For example, various substances naturally radiate electromagnetic radiation that is able to optically interact with the ICE 414. In some embodiments, for example, the fluid 302 may be or otherwise include a blackbody radiating substance configured to radiate heat that may optically interact with the ICE 414. In other embodiments, the fluid 302 may be radioactive or chemo-luminescent and, therefore, radiate electromagnetic radiation that is able to optically interact with the ICE 414. In yet other embodiments, the electromagnetic radiation may be induced from the fluid 302 by being acted upon mechanically, magnetically, electrically, combinations thereof, or the like. For instance, in at least one embodiment, a voltage may be placed across the fluid 302 in order to induce the electromagnetic radiation. As a result, embodiments are contemplated herein where the electromagnetic radiation source 402 is omitted from the optical computing device 500.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. A system, comprising:
    a flow path containing a fluid, the fluid including a desired characteristic;
    a fluid separator coupled to the flow path and having an inlet for receiving the fluid and a discharge conduit for discharging the fluid after having undergone a separation process in the fluid separator;
    an optical computing device having an integrated computational element configured to optically interact with electromagnetic radiation and the fluid before the fluid enters the fluid separator and after the fluid exits the fluid separator and thereby generate optically interacted light, the integrated computational element comprising a plurality of alternating layers of two materials having different index of refraction, the thickness of each layer and the number of layers being determined according to a spectral property of the electromagnetic radiation and a regression vector associated with the desired characteristic of the fluid, wherein a portion of the optically interacted light is transmitted through the integrated computational element; and
    at least one detector arranged to receive the optically interacted light and generate an output signal corresponding to the desired characteristic of the fluid.

2. The system of claim 1, further comprising an optical light pipe that communicably couples the optical computing device to the fluid at or near the inlet of the fluid separator.

3. The system of claim 2, wherein the optical light pipe conveys the optically interacted light from at or near the inlet to the optical computing device.

4. The system of claim 2, wherein the optical computing device further comprises an electromagnetic radiation source configured to emit the electromagnetic radiation that optically interacts with the fluid.

5. The system of claim 4, wherein the optical light pipe conveys electromagnetic radiation from the electromagnetic radiation source to the fluid at or near the inlet.

6. The system of claim 1, wherein the optically interacted light comprises first and second beams of optically interacted light, the first beam of optically interacted light being conveyed to the optical computing device via the optical light pipe.

7. The system of claim 6, wherein the at least one detector time multiplexes the first and second beams of optically interacted light and the output signal comprises corresponding first and second output signals.

8. The system of claim 7, further comprising a signal processor communicably coupled to the at least one detector and configured to receive the first and second output signals and provide a resulting output signal.

9. The system of claim 8, wherein the resulting output signal is indicative of how the desired characteristic of the fluid changes between the inlet and the discharge conduit.

10. The system of claim 9, wherein the desired characteristic of the fluid is a concentration of a substance in the fluid.

11. The system of claim 10, wherein the substance is a hydrocarbon.

12. The system of claim 9, wherein the desired characteristic of the fluid is one or more chemicals or chemical compositions present in the fluid.

13. The system of claim 12, wherein the desired characteristic comprises a chemical or chemical composition selected from the group consisting of salts, precipitates, water, chemical tags, physical tags, metals, organic compounds, volatile organic compounds, additives, treatments, polymers, drugs, medicines, poisons, emulsion breakers, digester organisms, de-foaming agents, coalescing agents, flocculants, and any derivatives or combinations thereof.

14. The system of claim 9, wherein the desired characteristic of the fluid is a concentration of a biological organism.

15. The system of claim 8, further comprising an automated control system communicably coupled to the signal processor and configured to adjust one or more parameters of the fluid in response to the resulting output signal.

16. A method of determining a desired characteristic of a fluid, comprising:
    containing a fluid within a flow path;
    conveying the fluid to a fluid separator coupled to the flow path, the fluid separator having an inlet for receiving the fluid and a discharge conduit for discharging the fluid after having undergone a separation process in the fluid separator;
    arranging at least one optical computing device on the fluid separator, the at least one optical computing device having at least one integrated computational element and at least one detector arranged therein, and the at least one integrated computational element comprising a plurality of alternating layers of two materials having different index of refraction;
    optically interacting the at least one integrated computational element with electromagnetic radiation and the fluid at or near the inlet, thereby generating a first beam of optically interacted light corresponding to the desired characteristic of the fluid at or near the inlet;
    optically interacting the at least one integrated computational element with the electromagnetic radiation and the fluid at or near the discharge conduit, thereby generating a second beam of optically interacted light corresponding to the desired characteristic of the fluid at or near the discharge conduit, wherein the thickness of each layer and the number of layers in the integrated computational element are determined according to a spectral property of the electromagnetic radiation and a regression vector associated with the desired characteristic of the fluid, and wherein a portion of one of the first or second beams of optically interacted light is transmitted through the integrated computational element;

receiving the first and second beams of optically interacted light with the at least one detector; and generating an output signal with the at least one detector, the output signal being indicative of how the desired characteristic of the fluid changes between the inlet and the discharge conduit.

17. The method of claim 16, wherein optically interacting the at least one integrated computational element with the fluid at or near the inlet further comprises conveying via an optical light pipe the electromagnetic radiation from an electromagnetic radiation source, the optical light pipe communicably coupling the optical computing device to the fluid at or near the inlet.

18. The method of claim 16, wherein optically interacting the at least one integrated computational element with the fluid at or near the inlet further comprises conveying the first beam of optically interacted light to the at least one integrated computational element via an optical light pipe communicably coupling the optical computing device to the fluid at or near the inlet.

19. The method of claim 16, wherein the output signal comprises first and second output signals corresponding to the first and second beams of optically interacted light, the method further comprising:

receiving the first and second output signals with a signal processor communicably coupled to the at least one detector; and generating a resulting output signal with the signal processor.

20. The method of claim 16, further comprising time multiplexing the first and second beams of optically interacted light with the at least one detector in order to generate the first and second output signals.

21. The method of claim 16, further comprising conveying the resulting output signal to a user for consideration.

22. The method of claim 16, further comprising undertaking at least one corrective step with an automated control system when a concentration of the desired characteristic of the fluid surpasses a predetermined range of suitable operation, the automated control system being communicably coupled to the signal processor.

23. The method of claim 16, further comprising conveying a warning signal to a user when a concentration of the desired characteristic of the fluid surpasses a predetermined range of suitable operation.

* * * * *